United States Patent
Longmire et al.

(10) Patent No.: US 11,587,682 B2
(45) Date of Patent: Feb. 21, 2023

(54) METHOD AND SYSTEM TO INTEGRATE DATA, ANALYZE AND DEVELOP IMPROVED CARE PLAN FOR A PATIENT AT HOME

(71) Applicant: Medable Inc., Palo Alto, CA (US)

(72) Inventors: Michelle Longmire, Palo Alto, CA (US); Ingrid Oakley-Girvan, Henderson, CA (US); Nick Moss, Los Alamos, NM (US)

(73) Assignee: Medable Inc., Palo Alto, CA (US)

( * ) Notice: Subject to any disclaimer, the term of this patent is extended or adjusted under 35 U.S.C. 154(b) by 0 days.

(21) Appl. No.: 17/200,866

(22) Filed: Mar. 14, 2021

(65) Prior Publication Data

US 2021/0358627 A1 Nov. 18, 2021

Related U.S. Application Data

(60) Provisional application No. 63/025,397, filed on May 15, 2020.

(51) Int. Cl.
*G16H 50/20* (2018.01)
*G16H 80/00* (2018.01)
(Continued)

(52) U.S. Cl.
CPC ............. *G16H 50/20* (2018.01); *G16H 10/20* (2018.01); *G16H 10/65* (2018.01); *G16H 80/00* (2018.01)

(58) Field of Classification Search
CPC ........ G16H 50/20; G16H 10/20; G16H 10/65; G16H 80/00
(Continued)

(56) References Cited

U.S. PATENT DOCUMENTS

2001/0034615 A1 * 10/2001 Wilkinson ............. G16H 80/00
705/2
2007/0033072 A1 * 2/2007 Bildirici ................. G09B 19/00
434/262
(Continued)

FOREIGN PATENT DOCUMENTS

WO   WO-2013036677 A1 *  3/2013   ......... G06F 19/3418
WO        2016110804 A1    7/2016
WO   WO-2016110804 A1 *  7/2016   ............... A61B 3/16

OTHER PUBLICATIONS

C. Stamate et al., "Deep learning Parkinson's from smartphone data," 2017 IEEE International Conference on Pervasive Computing and Communications (PerCom), 2017, pp. 31-40, doi: 10.1109/PERCOM.2017.7917848. (Year: 2017).*
(Continued)

*Primary Examiner* — Joy Chng
(74) *Attorney, Agent, or Firm* — Cesari and McKenna, LLP

(57) ABSTRACT

A method and system for connecting, capturing, managing and predicting outcomes for an improved care for home based patients by collecting data from caregivers and home-based patients. The method and system implemented as a mobile technology is more efficient and effective method for delivering healthcare that will ease the caregiving burden. Providing resources and information to communicate, capture and deliver by the caregivers (formal and informal), patients and healthcare providers communicate helps integrate essential data and care. Through the use of this mobile technology and associated devices vital information from informal caregivers, which is currently not regularly used in remotely located patients, can be captured and implemented in the decisions and adjustments to patients' care plans. In addition, the technology helps with adherence of patient specific treatment guidelines for home-based patients.

13 Claims, 18 Drawing Sheets

(51) Int. Cl.
*G16H 10/65* (2018.01)
*G16H 10/20* (2018.01)

(58) Field of Classification Search
USPC .......................................................... 705/2–3
See application file for complete search history.

(56) References Cited

U.S. PATENT DOCUMENTS

| | | | |
|---|---|---|---|
| 2009/0187425 A1* | 7/2009 | Thompson | G06N 5/04 703/11 |
| 2010/0268551 A1 | 10/2010 | Mcnames | |
| 2013/0080425 A1 | 3/2013 | Kwete | |
| 2014/0052465 A1 | 2/2014 | Madam | |
| 2014/0257852 A1* | 9/2014 | Walker | G06Q 10/10 705/3 |
| 2016/0242690 A1 | 8/2016 | Principe | |
| 2017/0109475 A1 | 4/2017 | Kaditz | |
| 2017/0140119 A1 | 5/2017 | Laha | |
| 2017/0235894 A1 | 8/2017 | Cox | |
| 2017/0286622 A1* | 10/2017 | Cox | G16H 50/30 |
| 2017/0372029 A1* | 12/2017 | Saliman | G16H 10/60 |
| 2018/0113988 A1 | 4/2018 | Desgranges | |
| 2019/0096511 A1* | 3/2019 | Longmire | G06F 7/00 |
| 2020/0303047 A1* | 9/2020 | Bostic | G16H 50/50 |
| 2020/0375544 A1 | 12/2020 | Naveh | |
| 2021/0142910 A1 | 5/2021 | Hafez | |
| 2021/0183518 A1 | 6/2021 | Karakaya | |
| 2021/0375459 A1 | 12/2021 | Longmire et al. | |

OTHER PUBLICATIONS

Yoon et al., The Clustered AGgregation (CAG) Technique Leveraging Spatial and Temporal Correlations in Wireless Sensor Networks, ACM Transactions on Sensor Networks, vol. 3, No. 1, Article 3, 2007, 39 pages.

Nasoz et al., Emotion recognition from physiological signals using wireless sensors for presence technologies, 2004, Cogn Tech Work vol. 6, pp. 4-14 (Year:2004).

International Search Report and Written Opinion dated Jun. 23, 2021, for International Application No. PCT/US2021/025259 filed Mar. 31, 2021 for Medable Inc.

* cited by examiner

| update | $0<br>Pregnancies<br>real<br>M: 3.25781<br>S: 3.13413 | $1<br>Glucose<br>real<br>M: 106.03<br>S: 32.8742 | $2<br>BloodPressure<br>real<br>M: 60.5677<br>S: 19.4745 | $3<br>SkinThickness<br>real<br>M: 18.1107<br>S: 15.0781 | $4<br>Insulin<br>real<br>M: 70.5872<br>S: 106.472 | $5<br>BMI<br>real<br>M: 28.1264<br>S: 8.05166 | $6<br>DiabetesPedigreeFunction<br>real<br>M: 0.412294<br>S: 0.308644 | $7<br>Age<br>real<br>M: 28.8893<br>S: 11.7129 | $9<br>k<br>categorical<br>N: 2 |
|---|---|---|---|---|---|---|---|---|---|
| delete | | | | | | | | | |
| @0 | 6.0 | 148.0 | 72.0 | 35.0 | 0.0 | 33.6 | 0.627 | 50.0 | 0 |
| @1 | 1.0 | 85.0 | 66.0 | 29.0 | 0.0 | 26.6 | 0.351 | 31.0 | 1 |
| @2 | 8.0 | 183.0 | 64.0 | 0.0 | 0.0 | 23.3 | 0.672 | 32.0 | 0 |
| @3 | 1.0 | 89.0 | 66.0 | 23.0 | 94.0 | 28.1 | 0.167 | 21.0 | 1 |
| @4 | 0.0 | 137.0 | 40.0 | 35.0 | 168.0 | 43.1 | 2.288 | 33.0 | 1 |
| @5 | 5.0 | 116.0 | 74.0 | 0.0 | 0.0 | 25.6 | 0.201 | 30.0 | 1 |
| @6 | 3.0 | 78.0 | 50.0 | 32.0 | 88.0 | 31.0 | 0.248 | 26.0 | 1 |
| @7 | 10.0 | 115.0 | 0.0 | 0.0 | 0.0 | 35.3 | 0.134 | 29.0 | 0 |
| @8 | 2.0 | 197.0 | 70.0 | 45.0 | 543.0 | 30.5 | 0.158 | 53.0 | 0 |
| @9 | 8.0 | 125.0 | 96.0 | 0.0 | 0.0 | 0.0 | 0.232 | 54.0 | 0 |

FIG. 7B

METHOD AND SYSTEM TO INTEGRATE DATA, ANALYZE AND DEVELOP IMPROVED CARE PLAN FOR A PATIENT AT HOME

CROSS REFERENCE TO RELATED APPLICATION

The instant application claims priority to U.S. Provisional application 63/025,397 filed on 15 May 2020. We incorporate all the limitations of the provisional application in its entirety.

STATEMENT REGARDING FEDERALLY SPONSORED RESEARCH OR DEVELOPMENT

This invention was made with government support under SBIR Grant No. HHSN261201700030C awarded by the National Institutes of Health. The Government has certain rights in the invention.

FIELD OF TECHNOLOGY

This disclosure relates generally to a field of a method and system for utilizing collected caregiver data, patient and physicians to develop improved care plans for patients at home.

BACKGROUND

Today's healthcare system contains much inefficiency that does not utilize easily available resources. These inefficiencies include, but are not limited to collecting and utilizing the best available data, healthcare spending waste, failing to involve all parties involved in a patient's treatment experience and not using existing technologies to capture patient's relevant data while they are in remote locations, like the patient's home. Some of the main causes for these inefficiencies include failure to coordinate care and the unnecessary complexity of our current antiquated health care system. In this regard, our existing healthcare is incredibly limited and not implemented in a way that can yield improved outcomes for all types of patient treatment, including for patients in clinical trials and patients receiving care at home. As a result, our current healthcare system is highly dependent on the individual patient's treatment at a "traditional brick and mortar" facility, whether it be a doctor's office, clinic, clinical-trial site, hospital/emergency room, or the like, which is unnecessary and results in a lot of valuable data never being captured, used or assessed. In addition, our current healthcare system is overly dependent on the patient's judgment of if and when they will even seek treatment at one of these at a "traditional brick and mortar" facility, which is another unnecessary inefficiency. In addition, the patient may forego or delay seeking treatment, possibly due to medical ignorance, fear of seeking healthcare, cost constraints or some other factor that in turn causes a medical condition to substantially worsen when it could have otherwise been prevented or more easily treated.

This litany of inefficiencies results in the delivery of uncoordinated healthcare and causes critical patient data to become fractured and decentralized. In addition, critical patient data becomes much less considered in its entirety when treatment options are considered. Moreover, since current means of healthcare are ultimately delivered through "traditional brick and mortar" facilities, there is often substantial waste of healthcare resources. Plus, the current healthcare system, wrought with these inefficiencies, does not specifically address patients being treated in a remote, home-based and/or clinical-trial setting.

There is a need to update and integrate the system to provide more efficient approaches and save resources and time.

SUMMARY

Several embodiments for a system and method towards developing care plans for home-based patients' collected caregiver data, utilizing plurality of mobile technology platforms, applications and devices are disclosed. In certain embodiments the disclosed system and method include implementing a plurality of mobile applications on a smart software system that caregivers will use to develop and implement home-based care, wherein home-based care includes at least care provided to patients outside of the clinical setting, for patients being treated for chronic diseases, such as cancer. The caregivers may be independent or be part of a care team. Caregivers may include informal caregivers (i.e. family and friends of the patient who give care without compensation). Such informal caregivers can be a vital source of data regarding the treated patients' safety and can heavily influence whether patients continue to pursue and adhere to medical treatment especially when the patient is being treated in a remote, home-based and/or clinical-trial setting. In addition, these informal caregivers are a wealth of information that is often not captured or detected by more traditional healthcare providers and caregivers of the patient, especially as it related to patients' symptom development that can ultimately lead to adverse events and potential clinical trial drop out.

In certain embodiments the disclosed system and method includes utilizing mobile applications allowing the patients' informal caregivers to track patient outcomes and provides informal caregivers guidance through resources relevant to the patient treatment, care and positive treatment outcomes. The disclosed mobile application is enabled to collect data directly from the informal caregivers about themselves and their corresponding patients, which promotes increased engagement of all stakeholders, wherein "stakeholders" may include but are not limited to the clinical care teams, patients, caregivers, healthcare professionals treating the patient, and family and friends of the patient, associated with the various aspects of patients' treatment and improved treatment outcomes. Such increased engagement of all stakeholders provides enhanced abilities to plan and adjust care through an integrated and dynamic tool with resources and communication pathways at any stage in the patients' chronic disease treatment. wherein "caregiver" encompasses family and friends of the patient who provides care without compensation The foregoing and other objects, features and advantages of the present invention disclosed herein, as well as the invention itself, is designed to help alleviate informal caregivers' burdens associated with caregiving to patients with chronic diseases including at least improving the mental and physical wellbeing of the informal caregivers and associated home-based patients. In addition, the present invention disclosed herein, as well as the invention itself, is designed to facilitate and improve communication with patients' healthcare team, to improve patient outcomes including symptom reduction, early warning of adverse events and clinical trial and/or study drop out.

BRIEF DESCRIPTION OF THE DRAWINGS

Example embodiments are illustrated by way of example and not limitation in the figures of the accompanying drawings, in which like references indicate similar elements and in which:

FIGS. 7A and 7B show an execution of a machine learning model to output risk level predictions across patients are performed.

Other features of the present embodiments will be apparent from the accompanying drawings and from the detailed description that follows.

DETAILED DESCRIPTION

Instant disclosure allows collecting, configuring, analyzing and provide secure data for and by the specific care team to improve patient care. Advances in mobile technology have allowed a variety of tools to be developed that can specifically address the in house care inefficiencies in the healthcare system, and yield significantly to improve patient outcomes in all settings, included but not limited to patients being treated in a remote, home-based and/or clinical-trial setting. Such mobile technologies include at least the following Wi-Fi/cellular enabled computing mobile devices (i.e. the iPhone, iPad, Android and Windows mobile devices), patient wearables (i.e. any hands-free computing device that can be worn as accessories, embedded in clothing, implanted in the user's body, or embedded into any part of the user's body cavity, including the skin which is enhanced with the ability to collect send and receive data via the Internet). All of these technologies enable substantially improved abilities to collect, communicate, store and accurately assess larger quantities of data relevant to improved patient treatment and outcomes. This includes an enhanced communication means utilizing said technologies, which allows effective patient treatment to not be unnecessarily reliant on the patient traveling to "traditional brick and mortar" facility(s) (i.e. doctor's office, clinic, clinical-trial site, hospital/emergency room, etc.). Such mobile computer applications and platforms can be used to yield substantially improved outcomes for home-based care patients with chronic disease, such as cancer, diabetes, asthma, Alzheimer's etc.

Several method, process and systems for capturing of plurality of remotely located data associated with patients' chronic disease treatment, utilizing mobile technology applications and associated devices, which leads to a substantial reduction in caregiver and healthcare-provider burden, improved care team communication and coordination, and offers opportunities to improve caregivers', patients' and survivors' mental and physical health and wellbeing, as well as provide important data on measures such as outcomes and quality of life. Utilization of the disclosed invention's embodiments results in significantly improved efficacy in reducing adverse events for patients in traditional medical treatment, clinical trials or research studies, as well as catching symptoms earlier which reduces costs associated with chronic disease treatment and enables swift resolution.

Figure 1:
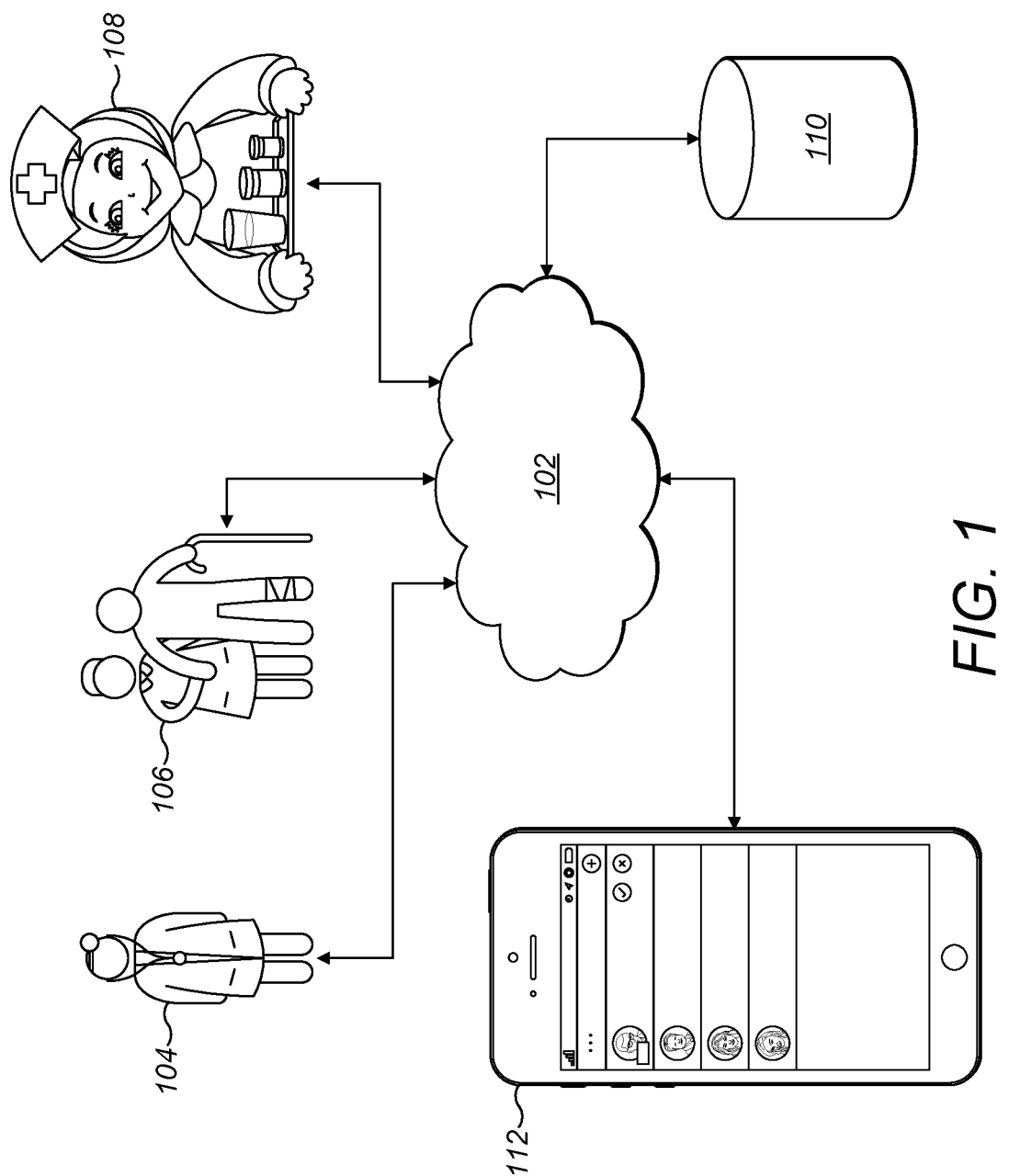
FIG. 1 shows a whole system approach to connect various stake holders.

FIG. 1 shows a whole system approach to connect various stake holders, cloud based analysis systems, databases and mobile devices being used by this technology. A physician 104, a patient 106 and a caregiver 108 form a specific closed know team that use a mobile device 112 to connect, share, communicate, present and get feedback. A cloud based and internet based 102 connectivity allows them to store the data in a database 110. Various modules and methods support the underlying architecture and process which will be discussed below.

Figure 2:
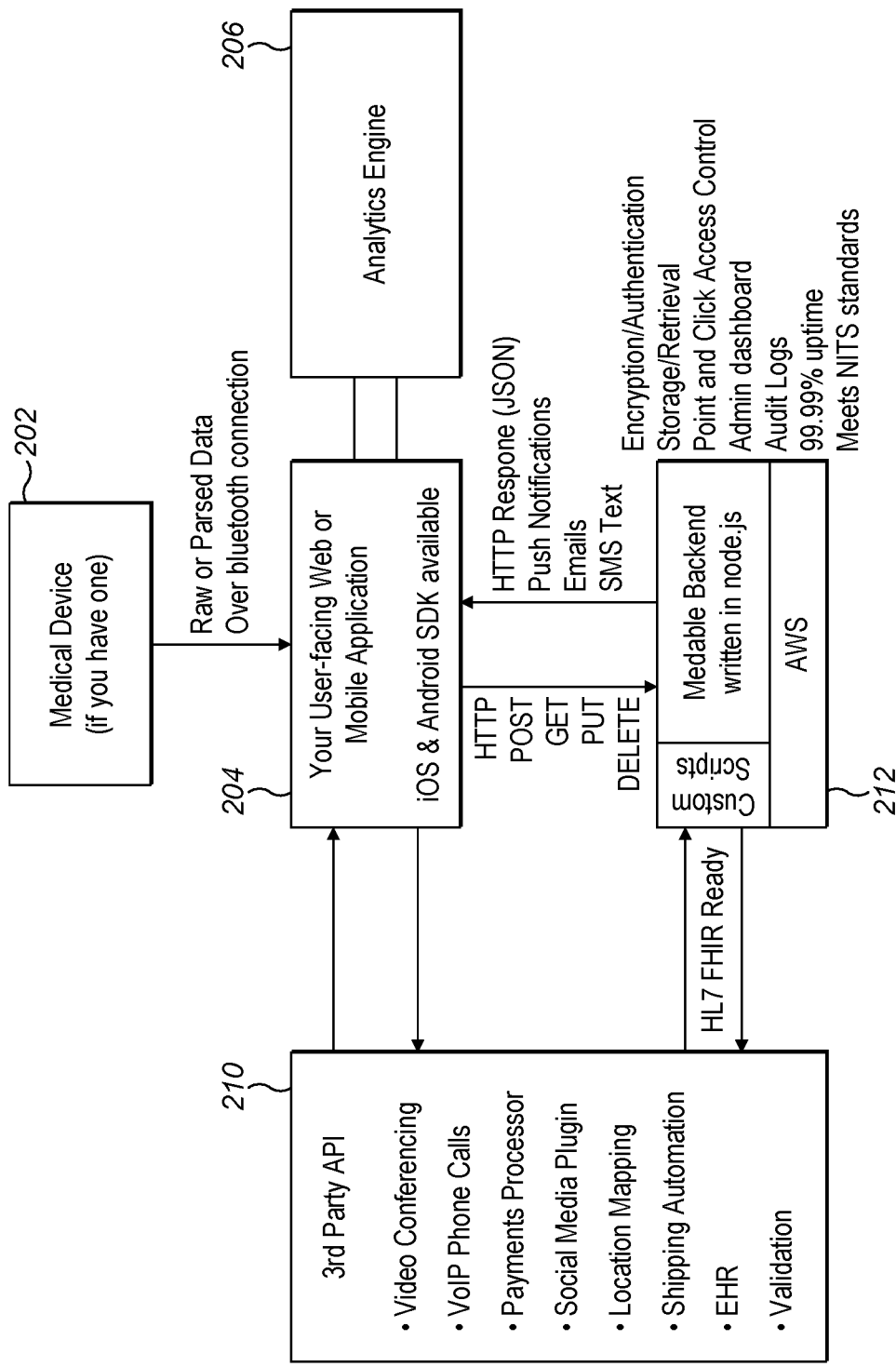
FIG. 2 shows a flow chart of system and method for providing an improved patient care

FIG. 2 shows a flow chart of system and method for providing an improved patient care by integrating patient, caregivers and physicians as a platform. The patient, caregiver and physicians have secured mobile devices 202 that convey the raw and parsed data to and from mobile device based application 204 to the analysis engine 206 and from third party API 210. The data gathered from all these interface is fed into instantly claimed backend analytical engine 212. The system and analytical engine perform various tasks such as encryption, storage, analysis, audit, Health Insurance Portability and Accountability Act (HIPPA) compliance of strict standards for all outside facing devices, connecting with patient data and most importantly presenting an outcome to the caregiver, physician and patient for a change in condition.

Figure 3:
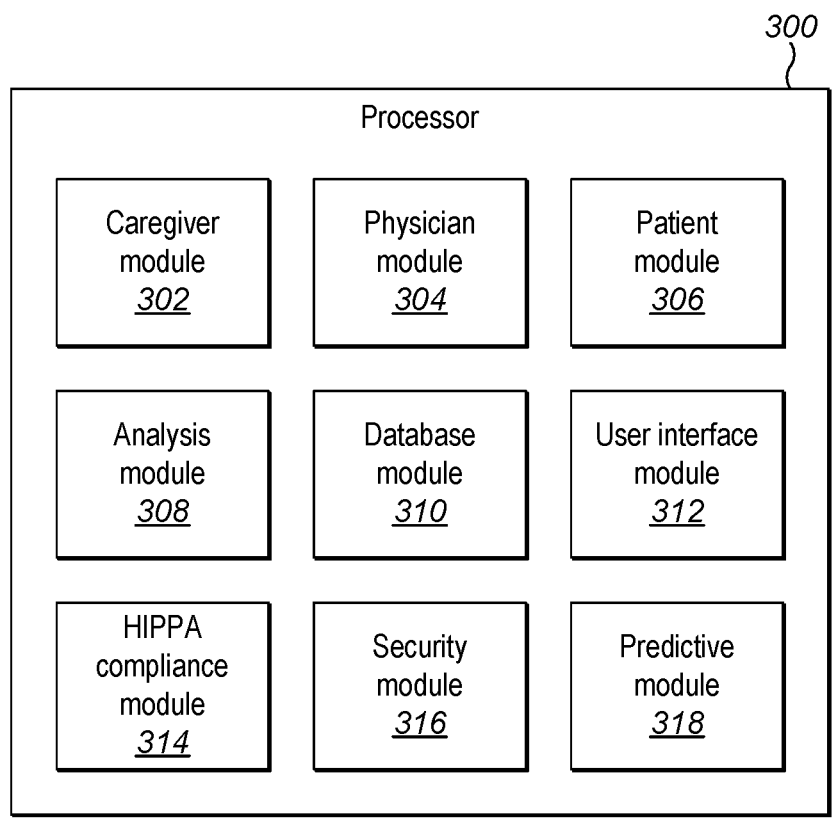
FIG. 3 shows different modules used in the system.

FIG. 3 shows different modules used in the system. The system architecture on a processor 300 includes several modules where metadata is captured, multi-directional communication abilities across stakeholder categories, provision of a dynamic care plan and automatic update methods possible through EHR and patient portal integrations. A caregiver module 302, a physician module 304 for the physician to input and retrieve data, a patient module 306 for the patient to input data and receive care plan from other stake holders, an analysis module 308 to analyze several data gathered from other modules and use algorithms to present critical feed back data for the patient, a database module 310 to store, partition, and provide data for analysis for an improved patient care, User interface module 312 to provide visualization, input and communicate within the specific care team and stakeholder specific data visualizations such as dashboards to optimize stakeholder usability, feedback, reporting for both clinical and research uses. A caregiver may be untrained professionals, family members or trained professionals who are given access to upload and communicate using the system regarding the patient health and get directives from physicians. A caregiver module 302 allows the caregiver to input data on a mobile device by observing the patient, their medication and daily routine. A physician module 304 allows a physician included in the specific care team to prescribe treatment plan to the patient, observe cohort analysis and communicate with other specific care team members in real time.

A security module 316 for following NCI's standard patient/provider/caregiver point of views, data security standards that meet NIH HIPAA standards at all data levels (a HIPPA compliant module 314 that), most importantly a predictive module 318 using various algorithms to provide for possible downtrends in the patient profile or improvements in the patient profile for the specific care group. Caregiver and patient education and other content within mobile applications is easily included via integration with application programming interfaces (APIs) to provide the content through backend systems that contain the material of interest, or via embedded selected URLs. This is enabled by the instant system underlying architecture. The patient module 306 allows the patient to input data, check on treatment plan suggested by the physician, gather information about other resources such as ride share etc., and communicate securely with other specific care team such as nurses and family members.

Information about potential symptoms and treatment and resources in the community:
  Using personalized analytics, an algorithm can be established to provide information that is based on specific symptom related data. For example, if a patient with breast cancer reports lymphedema, information about this condition and next steps can be intelligently provided in the application to the caregiver and the patient.
  Links to information for the caregiver/patient on transportation, respite care, etc., Videos about infusion ports and other aspects of patient specific treatments are also given.
  Using preset features according to clinical guidelines or personalized analytics, an algorithm can be established to provide information that is based on data linked from the EHR such as if a patient has been prescribed an infusion port or based upon caregiver and patient reported feedback.
  Specific care guidelines and disease-related information
  Using the platform, disease-specific information and educational resources can be displayed in the application. This information can come from API integration with existing content systems and can be personalized using the personalized analytics system. This can also be extended to include therapy/counseling resource instructional videos on specific topics and more. There are many resources already developed at the federal/state or institutional level and these can be automatically included in the library of information.
  Specific information for caregivers such as resources for mental and physical wellbeing can be integrated directly through APIs to the original source or linked through direction to the providers' website.

Figure 4:
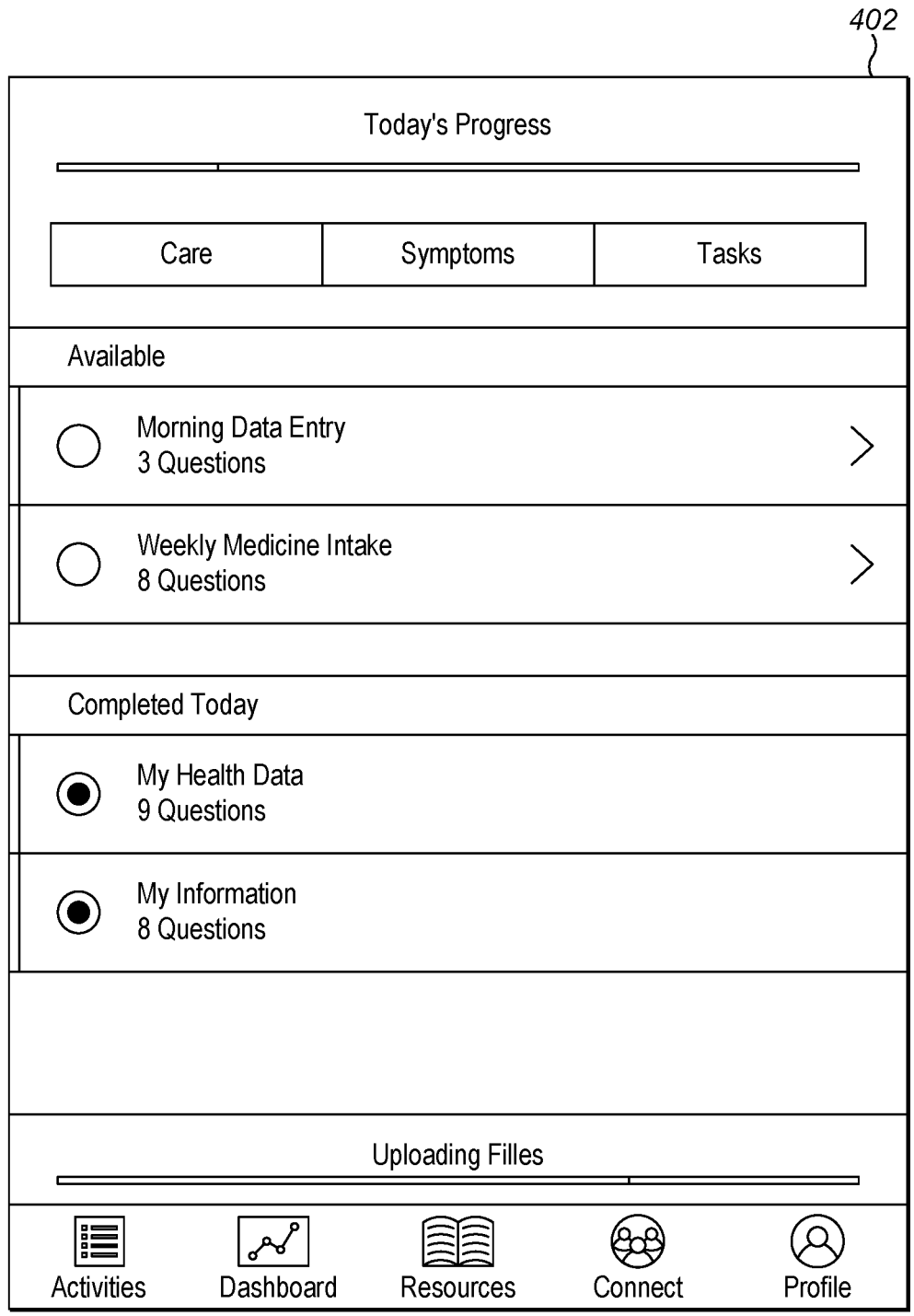
FIG. 4 is an example of one of the mobile device screen hosts showing that particular day progress.

FIG. 4 is an example of one of the mobile device screen hosts showing that particular day progress 402. It provides care, symptoms and tasks tabs. The patient, caregiver and physician can input the data and in real time the patient is able to see the directives and recommendations. Physician's alerts to Site feature in case of a potential adverse event might occur. The Care Event tab allows a health expert to define type of adverse event and then configure an alert type based on the type of response needed for the event (SMS, email, phone call). Due to patient's specific care team can communicate and data share together calendar features with medication, infusion ports/other device maintenance, other caregiving concerns, and trial visit reminders via the Alerts and Notification system. Medication alerts can be configured at the study level for all participants or can be enabled to be configured by the caregiver/participant directly. The mobile application can be configured to enable a user to securely share these notes, if this is a desired functionality.

Figure 5:
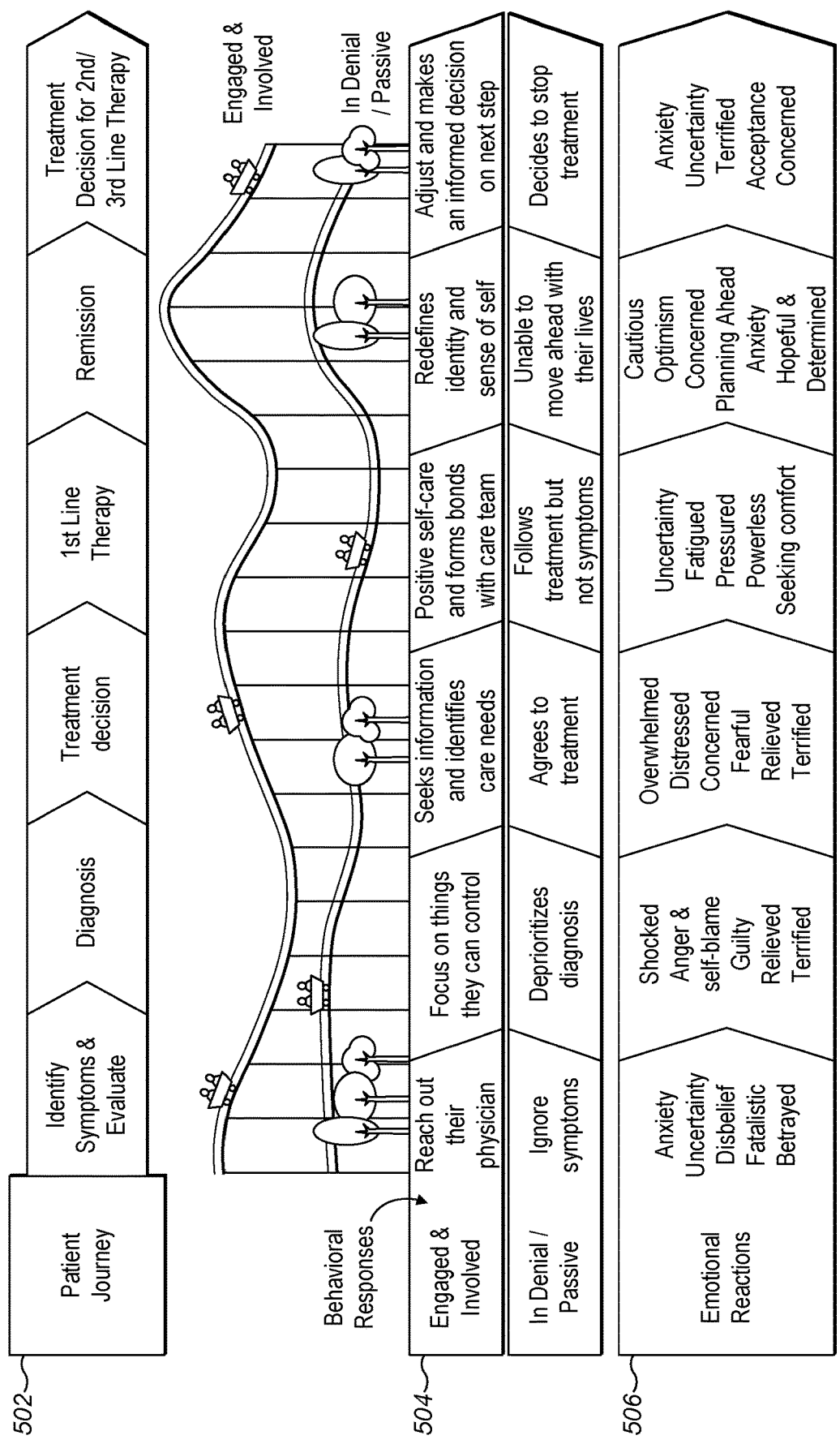
FIG. 5 shows an example of a patients journey through cancer treatment for example.

FIG. 5 shows a typical journey of a cancer patient from diagnosis to treatment (502). The behavioral responses (504) shows data points for various steps including engaged and involved or passive and/or denial state. The emotional reactions for every stage (506) are recorded for further analysis.

Figure 6:
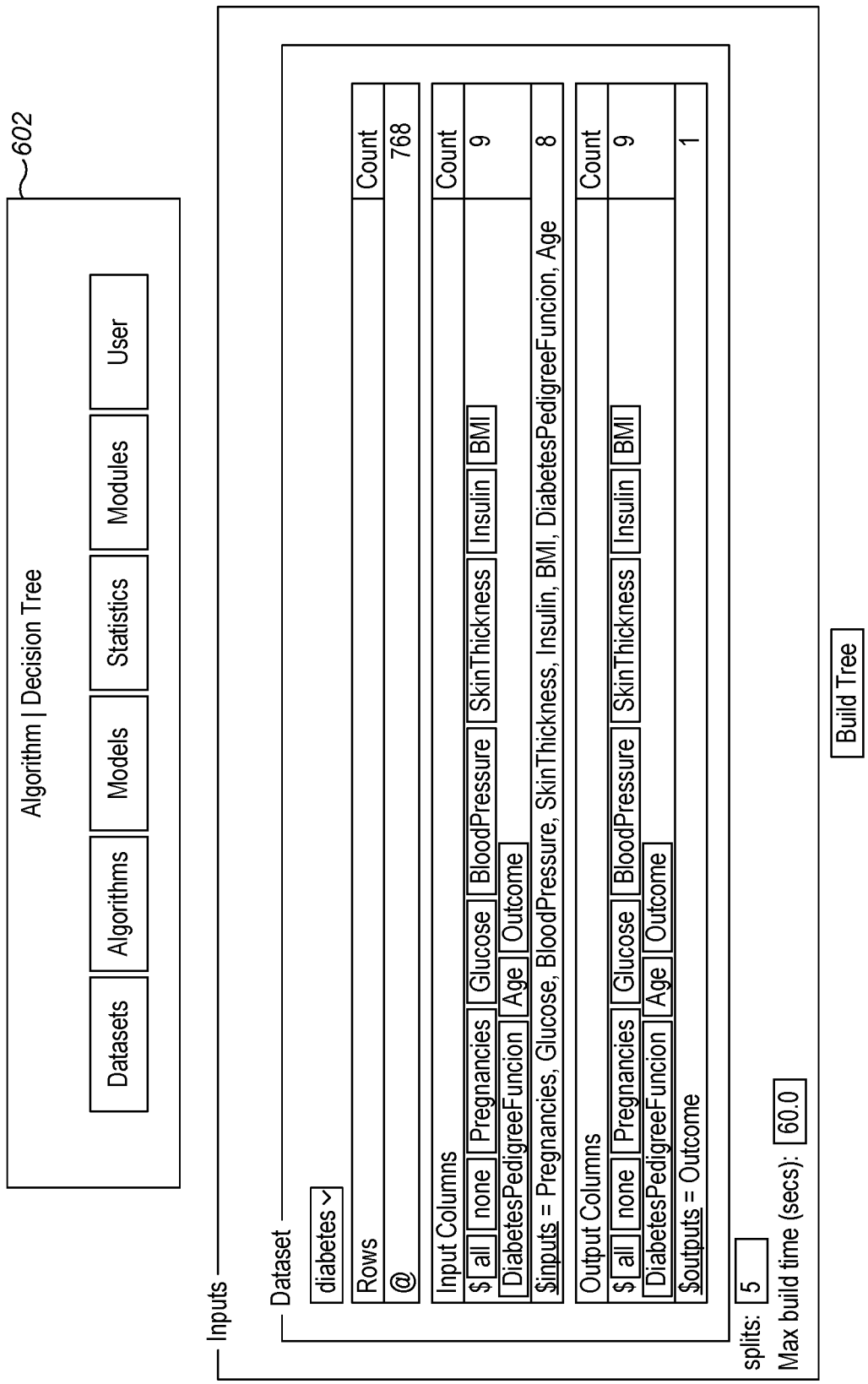
FIG. 6 shows rapidly evaluating and building different decision tree models with varying parameters to develop a risk model.

FIG. 6 shows rapidly evaluating and building different decision tree models with varying parameters to develop a risk model. This may be displayed as Trend and predictive analysis of symptoms in a dashboard showing Clinical Data Analysis Dashboard wherein a health expert can query data to see cohort trends and query across studies by demographic or study feature. This enables predictive analysis of patient data by using collected data over a sufficient time interval to develop pattern identification with artificial intelligence (regression analysis, neural networks, etc.).

Figure 7A:
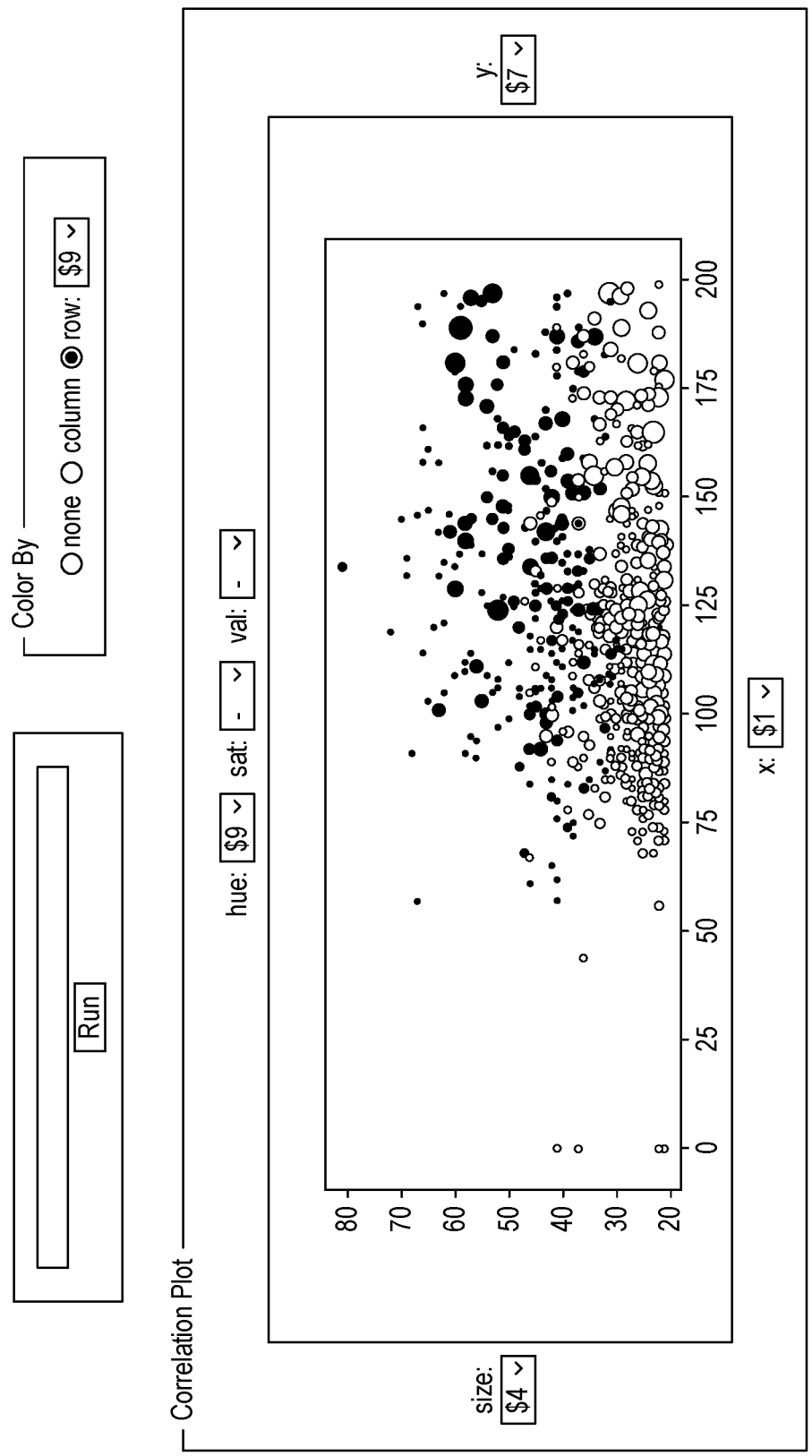

FIGS. 7A and 7B show an execution of a machine learning model to output risk level predictions across patients are performed. A key component of the system is a proprietary data standardization and normalization technology that ingests vastly varied data types e.g.: smartphone sensor, participant surveys, medical device, contextual, clinical study, and lab data. The system utilizes formats such as CSV, JSON, and HL7 for the import, export, and data interchange between various systems. The system and method generates machine learning models to enable pattern detection and algorithm development with the most sophisticated algorithms including deep learning, decision trees, Bayesian, and unsupervised methods such as clustering. To maximize efficiency, Analytical engine's data frame is binary compatible with popular machine learning formats and can support interchange between mainstream data science tools with minimal or no data copying. Furthermore, implementing instant method and system with Analytical engine provides the following key advantages:
  The system and method allows users of various data science experience levels to utilize the system using an interface which is most appropriate for their skills and preference. The system provides tools to allow power users to work with existing data science tools in a way that they are accustomed to, e.g. Python and R interfaces. The system allows usage of a combination of interfaces for solving a problem. The system and method provides rich ways of visualizing data. The system and method allows the computational system to scale while allowing for the ability to control costs of utilized computational resources. The system enables the modular implementation of multiple front-end interfaces, each custom-tailored to specific data analysis and machine learning tasks.

Figure 8:
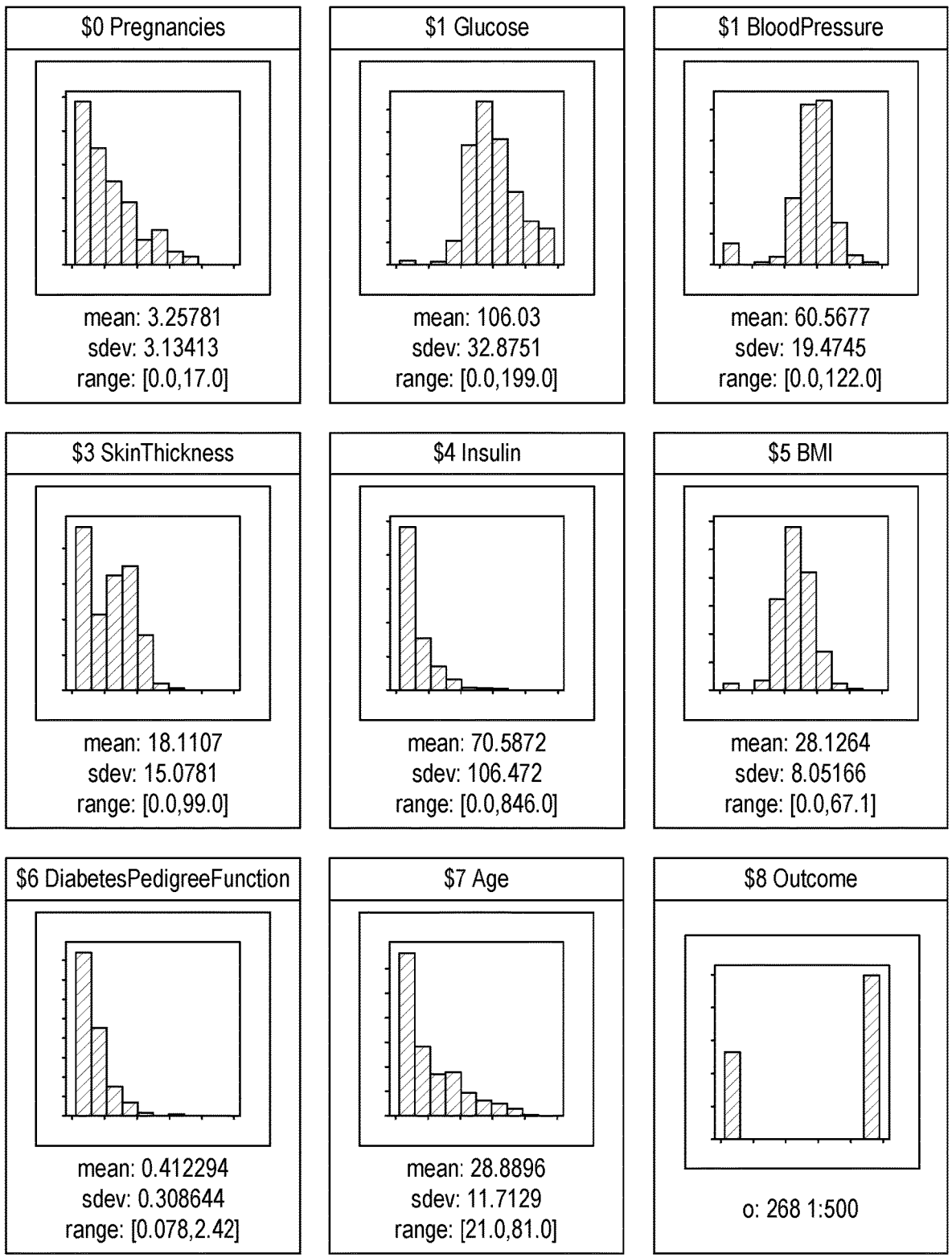
FIG. 8 shows viewing various data crunched using cohort data for various patient attributes.

FIG. 8 shows viewing various data crunched using cohort data for various patient attributes. The instant system, we developed separate portals that allow patients to visualize their health metrics vs. views for caregivers to manage groups of patient cohorts and to be alerted of pertinent patient events, for instance. On the other hand, for instant method and system data scientists, responsible for developing predictive models, using Analytical engine's RESTful interface as a backend, we have designed a high-level web interface that simplifies data exploration, data preparation, and machine learning model building tasks, making it easier for the non-data scientist expert to quickly perform such tasks. Furthermore, domain specific applications such as those developed for the instant method and system. These applications can be rapidly prototyped and deployed using this same system. Analytical engine streamlines and automates various data preparation stages with a domain-specific language called CML (Analytical engine Modeling Language) and through other easy-to-use graphical user interfaces. Data features, data transformations, and the results of training and running machine learning models are instantly visualized through the integrated UI. The analytical model either runs on a processor or is implemented as cloud computing technique.

An analytical engine's high-level web interface can be used side-by-side with lower-level programmatic methods. In other applications, Analytical engine has been leveraged to detect patterns in massive patient generated data sets and generate algorithms for disease prediction and digital biomarkers. We use Analytical engine to create standardized representations of different data types specific to instant method and system, ensuring highest quality data standards, and to provide the ability to create high-level tools and web interfaces to allow instant method and system participants to rapidly run various analyses, to observe patterns and trends in the data, and to extract key insights. We developed a custom high-performance database as part of Analytical engine that can be used to create standardized representations of the various data types of interest to instant method and system. We have deployed this database system to several applications. Our database system enables parallel queries to traverse large data sets and allows individual rows to contain free-form data. This feature is vital to capture of varying formats such as EMR or claims data and patient centric data. Also key to this approach is the ability to effectively capture metadata and index key parts of such data for later retrieval. Crucial to attaining high performance, is the ability to optimize schemas and handcraft queries to achieve optimal performance on large-scale data sets or smaller data sets where we need to traverse such data repeatedly to evaluate multiple possible model configurations. In our method we enable the user to create an interactive application to query hundreds of millions of patient records in real-time. We implement instant method and system following the software as a service (SaaS) approach where our database system can be securely queried behind a RESTful interface so that various front-end clients can access the data through a client agnostic API. We started with Analytical engine's existing data standardization tools and refined them to address specific requirements of the instant method and system application. Analytical engine's data tools can be used to ingest and standardize data sets in a variety of formats and can help to report missing values, distributions of categorical values, and statistical summary information and we can use Analytical engine's UI to further assess the structure of individual data sets of interest.

These tools can output a mapping configuration to automatically parse individual data sets. Following auto-mapping, typically, a small amount of manual intervention is then required to further fine-tune specific attributes of the data representations. For example, creating functions to properly handle various idiosyncrasies in the data, e.g. differing formatting of dates, null values, units, etc. Analytical engine's data summary tool can output a series of reports to allow early exploration of the data and enable us to create configurations for properly handling the mapping and ingestion of disparate data sources. Finally, from these mappings, Analytical engine can automatically generate schemas to ingest and map these disparate data sources into Analytical engine's high-performance database system. We use Analytical engine's data analytics and machine learning capabilities to analyze integrated data streams specific to instant method and system in a variety of ways. These data streams include: EHRs containing diagnosis data, age and other demographic information, and treatment/comorbidity history. After data sets have been standardized, we can run algorithms on the aggregated data to explore correlations and what can be predicted while identifying inputs necessary to make such predictions. Unsupervised methods such as clustering can be used to identify trends across patient groups and to identify key factors associated with the early onset of adverse events or to identify areas where data contains inconsistencies.

Analytical engine can also be used to ensure data integrity, especially when dealing with missing or incomplete data related to the collection of patient data. Deep learning models, using recurrent layers for instance, can be used for such purposes. Analytical engine's high-performance database system is ideal for traversing large sets of patient and filtering the data for specific criteria. Instant method and system uses the following machine learning algorithms: deep learning, clustering, decision trees/random forests, and Bayesian inference. With the exception of clustering, as we will be primarily using supervised machine learning for instant method and system, which relies on labeled data, the survey information we collect is designed to provide the labels needed for such predictions. These labels primarily include whether the patient is experiencing adverse events. The rest of the data collected can be used to generate models that can predict, before it happens, whether a patient is about to experience adverse event. Namely, our models will output a risk level associated with patients so caregivers can be alerted early. The model inputs are highly dimensional and will take into account a variety of inputs ranging from survey data, to EHR, to connected devices data. We normalize each kind of data separately, e.g. by z-scoring samples with respect to global statistics. We then combine the normalized features into a single "feature vector" per patient per unit of time, with the temporal resolution determined by the most frequently available source of data. Data that does not change with each minimum unit of time is simply repeated across feature vectors until it is updated with new values. This creates a time series representation for each patient, containing at every step all of the features we intend to use for downstream analysis.

Additionally, forecasting models can be trained to predict the evolution of patient state in time along these feature dimensions. Such approaches could be useful if the available features correlate to relevant physical symptoms (for example, fatigue might present itself in gait-speed and sit-and-stand tests). This could lessen the caregiver burden associated with monitoring. Relatedly, data could be passed to anomaly-detection models, which could alert caregivers to sudden and potentially alarming chances in patient state. When constructing the data frames, one of the key aspects is the ability to identify patients. Identifying information will be stripped from all instances of the patient data and each patient is assigned a unique ID to allow members within our group to work with the data in accordance HIPAA and other international privacy5 standards. While the beginning parts of data frame construction require manual work to properly encode continuous and categorical values, and to separate the data of interest for predictive purposes, later stages can leverage a variety of Analytical engine's automated capabilities. One such function is for Analytical engine to 1) analyze factors in common across patients and 2) perform a series of batch runs over the data to a)

determine which states can be predicted from other values, e.g. for determining patient risk sentinels b) perform a minimization and identify key predictors used for subsequent models. We designed the instant method and system prediction engine to be robust and self-adapting—as we collect more and more patient information, the system can tune itself to make increasingly better predictions. We will use specialized algorithms to analyze the data collected from the walk tests and the sit/stand tests. Because we expect the data collected from these to be less abundant than the rest of the data we are collecting, conventional methods like deep learning or decision trees/random forests will not be applicable as such algorithms typically require at least several thousand labeled samples in order to be a most effective.

These specialized algorithms we have developed for instant method and system allow us to map time-series data into a set of histogram frequencies that summarize the range, mean, variance, providing higher level statistics of connected devices data such as gyroscope or accelerometer. These are then tuned and inputted to a clustering algorithm which can then pinpoint abnormalities in gait, balance, etc. and provide a sentinel for at risk patients. On the unsupervised learning front, we can analyze cohorts of patients using clustering methods to isolate patients into groups according to those most likely to: —develop complications—demographic commonality—those require special care and extra attention—those requiring common standards of care These groupings of patients can be constructed both from: —the static demographic and personal information—time specific information, i.e. daily surveys These groups of patients can then be monitored separately in the front-end portal. Analytical engine provides the analytical and machine learning backend as a service and through its modular design allows various portals to be constructed, allowing caregivers and other stakeholders to monitor patient cohorts in real-time. The portal provides a quick status view of patients within a specific group or those assigned to a certain caregiver. Such views provide a simplistic view in aggregate whereby caregivers can at a glance gauge the status of patients, e.g. green light means everything is normal or red light and allows for drilling down to specific patients to allow the caregiver to determine for which reasons specific patients were flagged as being at risk. The portals can be easily specialized around a specific condition, e.g. diabetes or a specific type of cancer.

The system and method will allows capturing, monitoring and recording symptoms/side effects and quality of life indicators. Survey intervals and recurrence are defined by the health expert for the application. Surveys can capture any caregiver or patient reported information such as symptoms, side effects, quality of life measures and other issues.

The system provides intelligent algorithmic capabilities that enable automated treatment recommendations based on patient data. Using Care Rules, our health experts will create Care Rules, which is an intelligent algorithm that monitors the data and then sends the user a treatment recommendation when the data issue is encountered by the algorithm. The Care Rule can also drive recommendations and notifications to the Care Team that includes the caregiver.

On the Care Rule Console, the health expert can create custom Care Rules including custom notifications and treatment recommendations.

The Care Console is custom configured during the implementation to include the features needed for the clinical work. Once configured the Care Rule Console is used by a health expert.

Differentiator: We have the only healthcare application platform with configurable algorithm driven alerts, notifications, and recommendations.

Any device being used has to be integrated. Device data is critical to capturing rich longitudinal patient data, and is often an essential component of home monitoring. The system enables integration capabilities with wearables and sensors for biometric data collection and passive monitoring The Instant system and method platform is designed to capture, analyze, and visualize device data in real-time and to enable alerts and notifications from real-time continuous device data monitoring through Instant system and method Insights and Alerts.

Mobile applications developed on Instant system and methods are configured to include community features such as resources, support groups, locations for transportation information, respite etc. Many mobile apps built on Instant system and methods have community features that provide chat-based virtual communities where patients can connect anonymously to share experiences. As part of work plan we added virtual communities and support group resource links (urls/contact information) to the caregiver dashboard and this can be automatically updated by the administrator of the app as an upgrade delivered to the user.

The present invention relates to systems and methods in the remote healthcare treatment of chronic diseases in an environment that facilitates the management of the associated patients' treatment care plans, incorporating data from the plurality of associated caregivers and healthcare professionals. The disclosed invention involves collecting information regarding a patient's environment and physiological measurements associated with improved treatment outcomes utilizing vital sources of data from a plurality of stakeholders involved in treating patients with chronic disease. The data collected is processed in view of an existing medical care plan in order to facilitate automatic updating of the current care plan or selection of a new plan based on providing the information to remotely located patients and caregivers.

Figure 9:
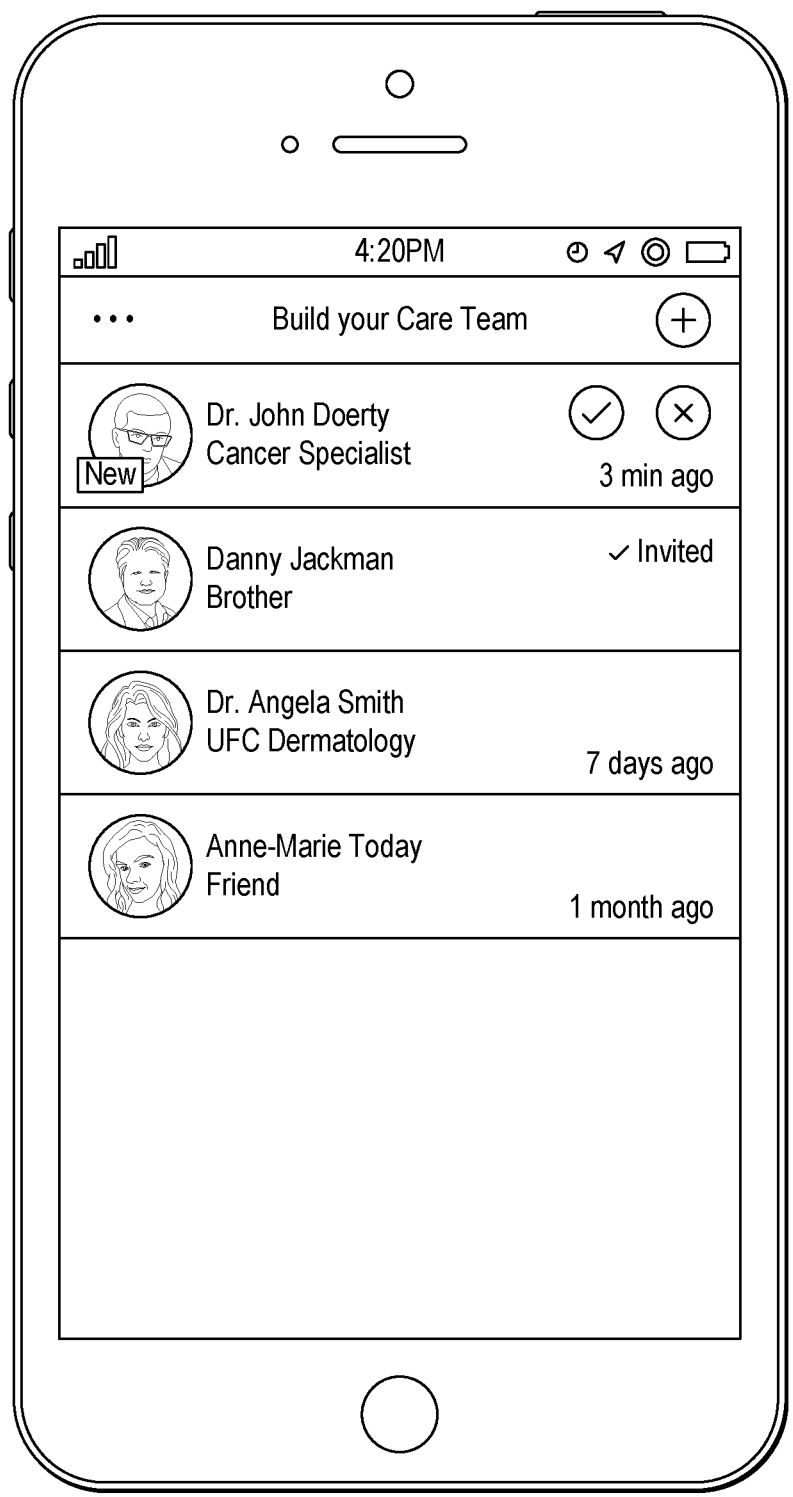
FIG. 9 shows a care team screen shot.

FIG. 9 shows a care team screen shot. This screen shows the patient builds and manages the care team. Patient enters app and invites healthcare providers by entering their email addresses. Provider can then download and view patient data, patient can also invite family members and surrogate decision makers to participate. Provider's side of the application enables management of multiple patients.

Figure 10:
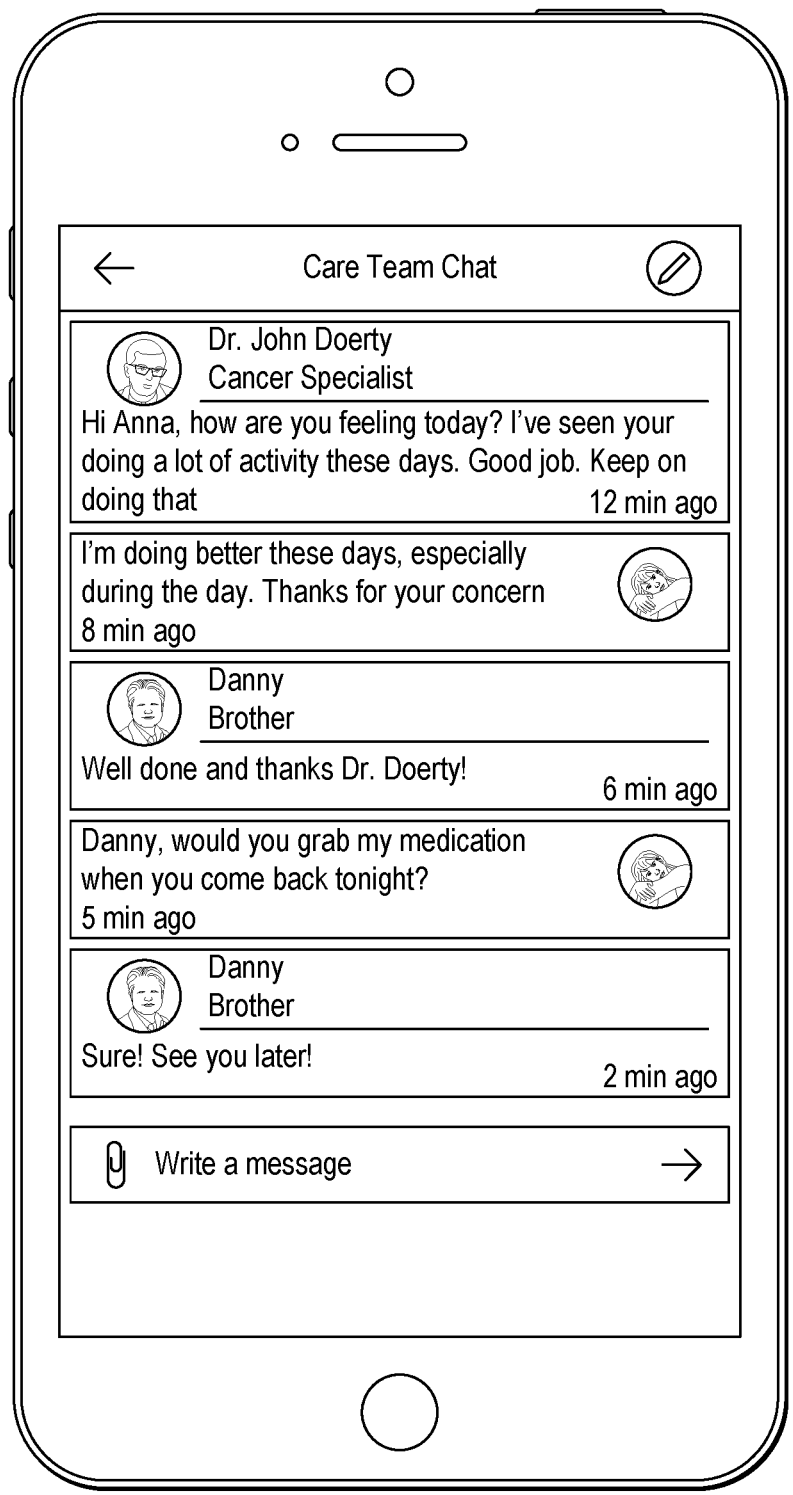
FIG. 10 care conversation screenshot.

FIG. 10 shows a care conversation screenshot. Uniting the providers from different institutions and departments enables seamless healthcare communication that is patient centered and team based care is shown. Users can share health data and documents using this forum in the same way that documents are shared on skype. Once the shared documents are available it can be viewed by the recipient. Users can unshare the documents at any time.

Figure 11:
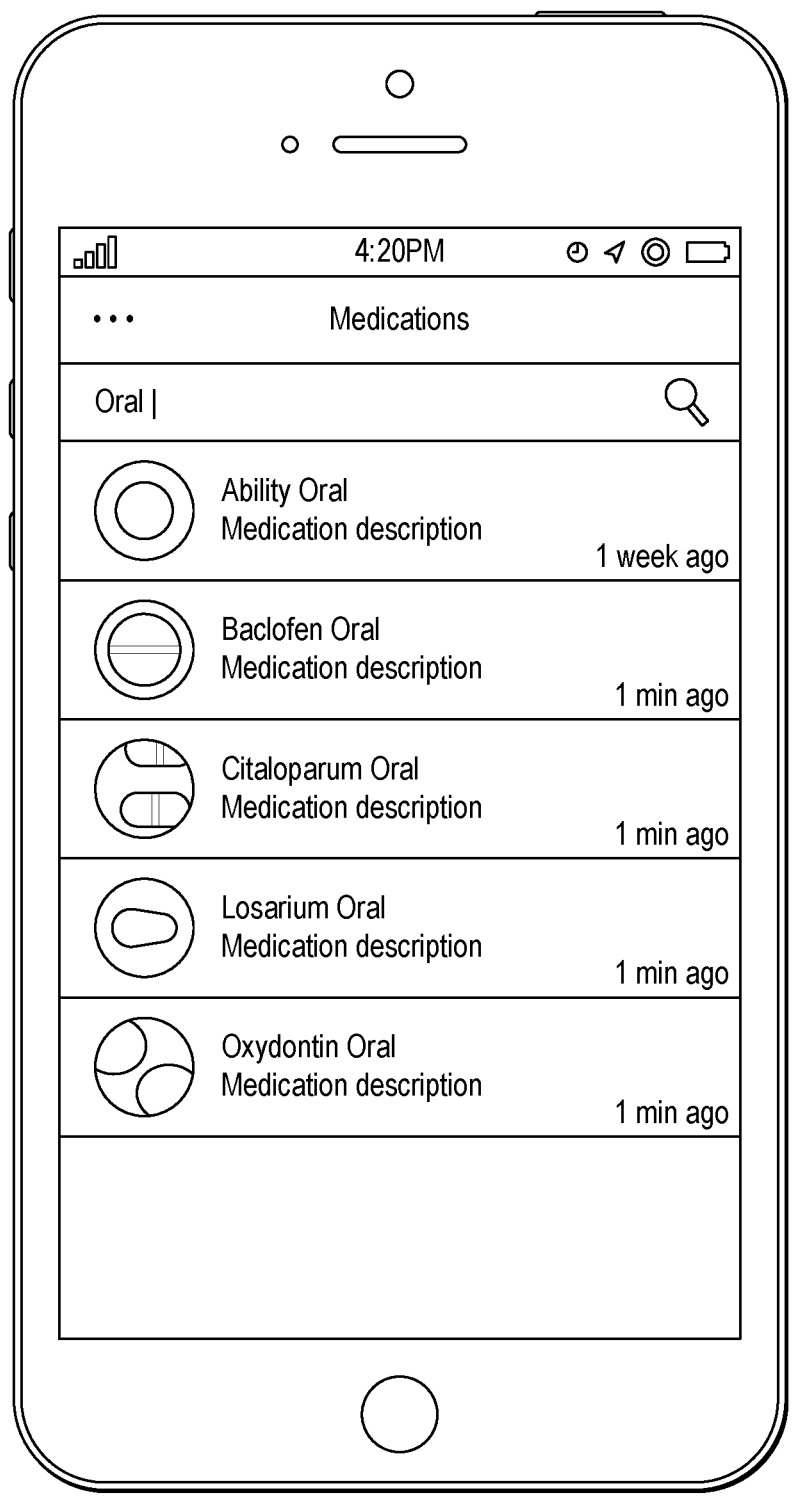
FIG. 11 is a pill finder screen shot.

FIG. 11 is a pill finder screen shot. This screen of the application shows images of the medications that the patient is taking or has been prescribed. The patient can easily search for medications. Integration with Surescripts API and EMR's enables automated prescriptions and refills. Proprietary medication-recognition software ensures that the patient has the proper medication and takes the medication at the right time of the day.

Figure 12:
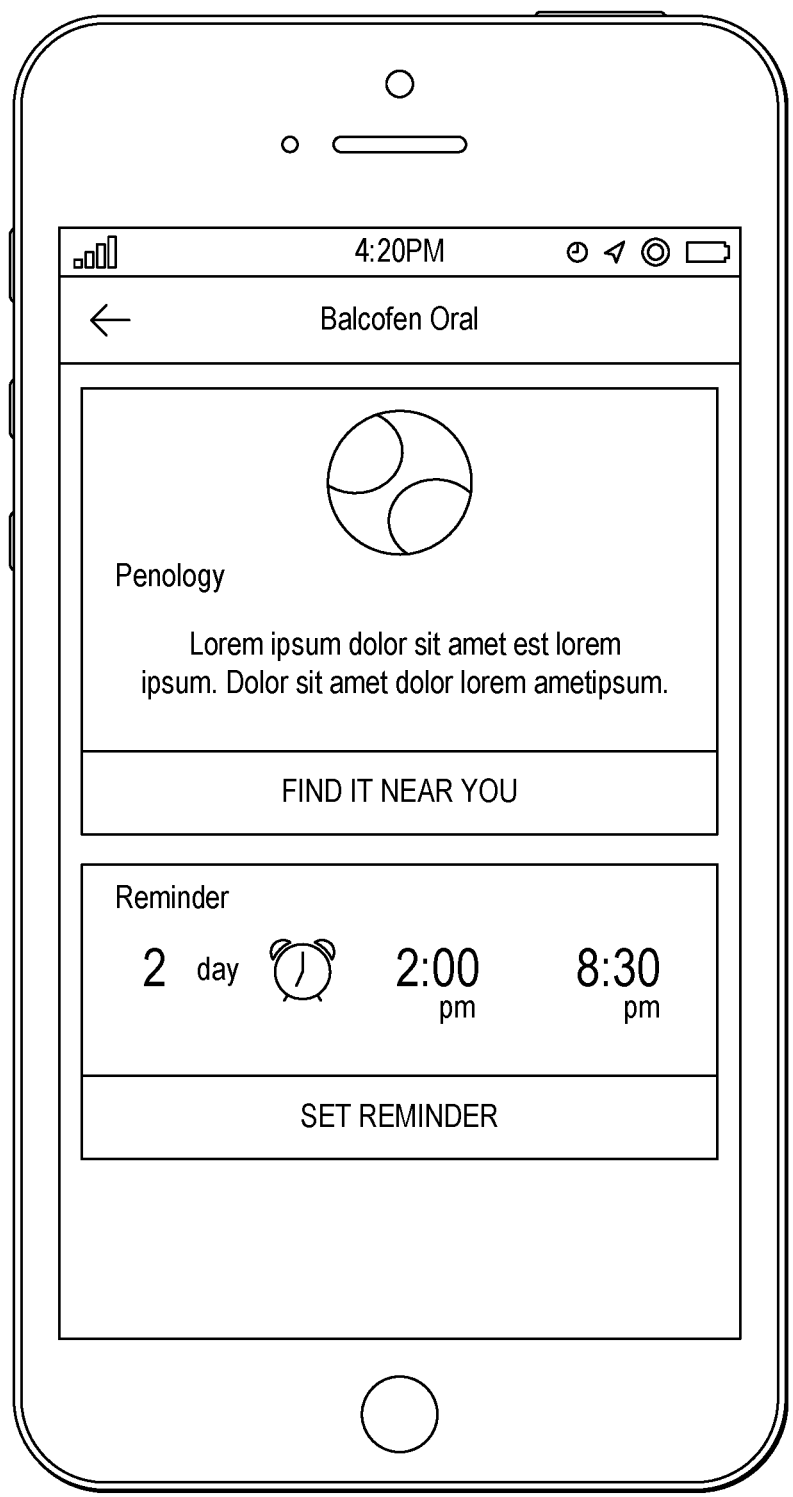
FIG. 12 medication reminder screen shot enables patient to set medication alerts.

FIG. 12 medication reminder screen shot enables patient to set medication alerts and reminders, it is easy to design, the schedule can be set by patient or care partners for automated reminders, and proprietary computer vision technology can verify proper pill combinations taken at appropriate time of day. In addition, the present invention results in increased retention and adherence from home-based patients when they are at home.

Figure 13:
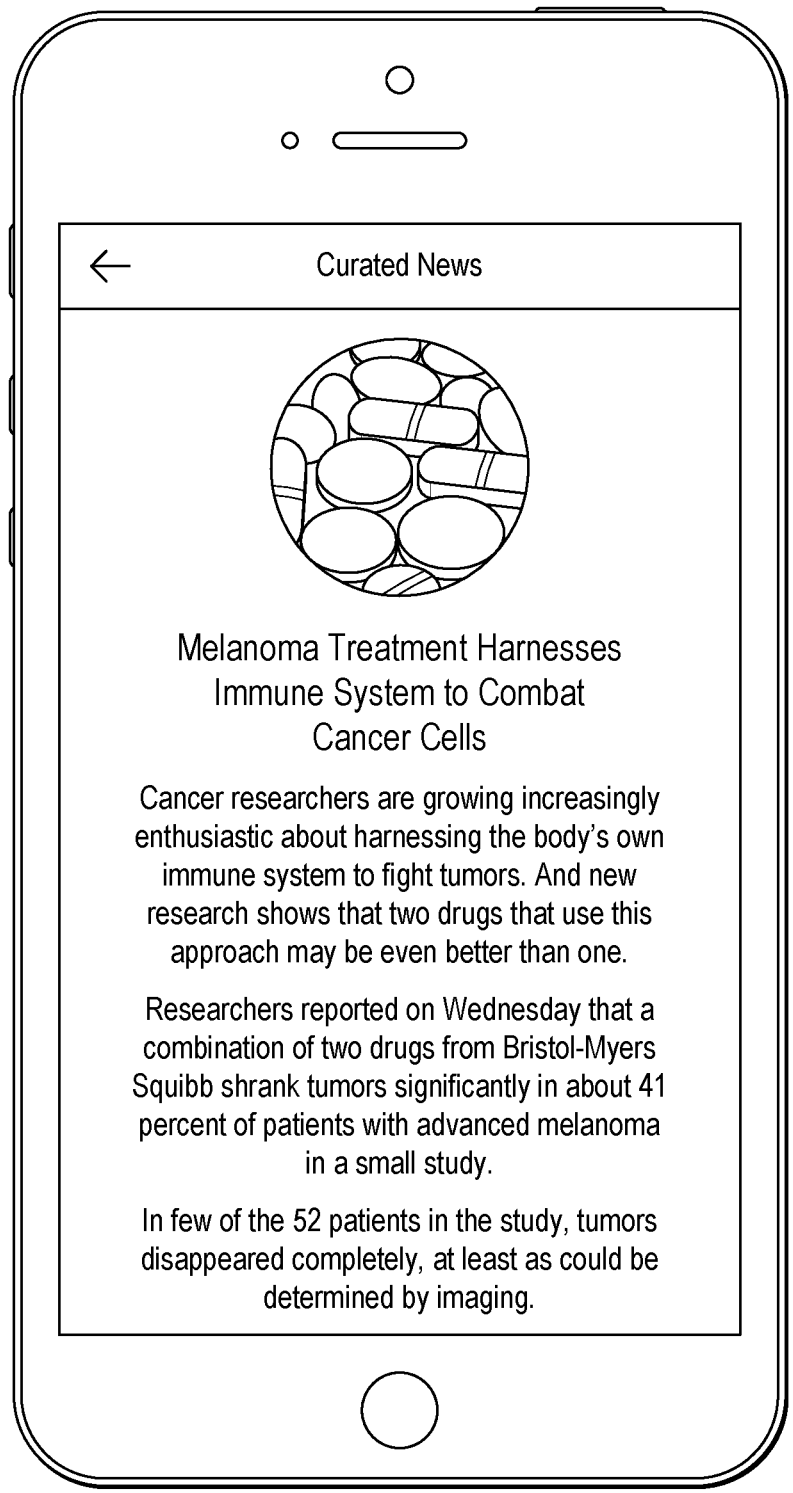
FIG. 13 is health information for caregiver or patient screen shot.
Figure 14:
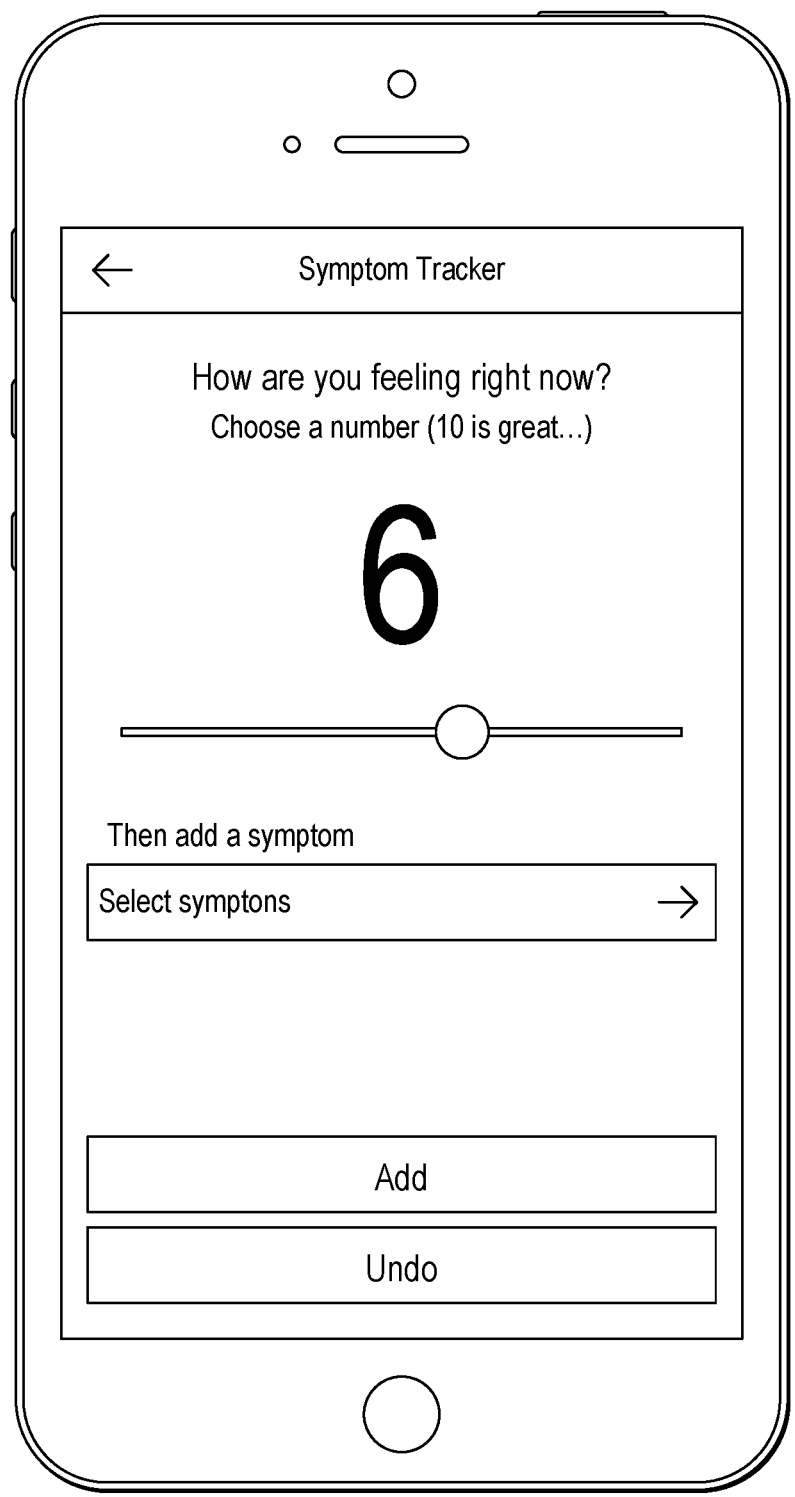
FIG. 14 shows a symptom tracker screenshot.

FIG. 13 is health information for caregiver or patient screen shot. This enables the technology to intelligently combine information from the EHR (Diagnosis, age, treatment history and comorbidity data) to provide curated health information. News and research related to survivorship and specific disease is displayed. FIG. 14 shows a symptom tracker screenshot. The patient may be prompted to enter his/her energy level and any symptoms he/she is having. Using voice or text or easy data entry, the patient enters energy level as well as any specific symptoms. This history is shared with the specific care team.

Figure 15:
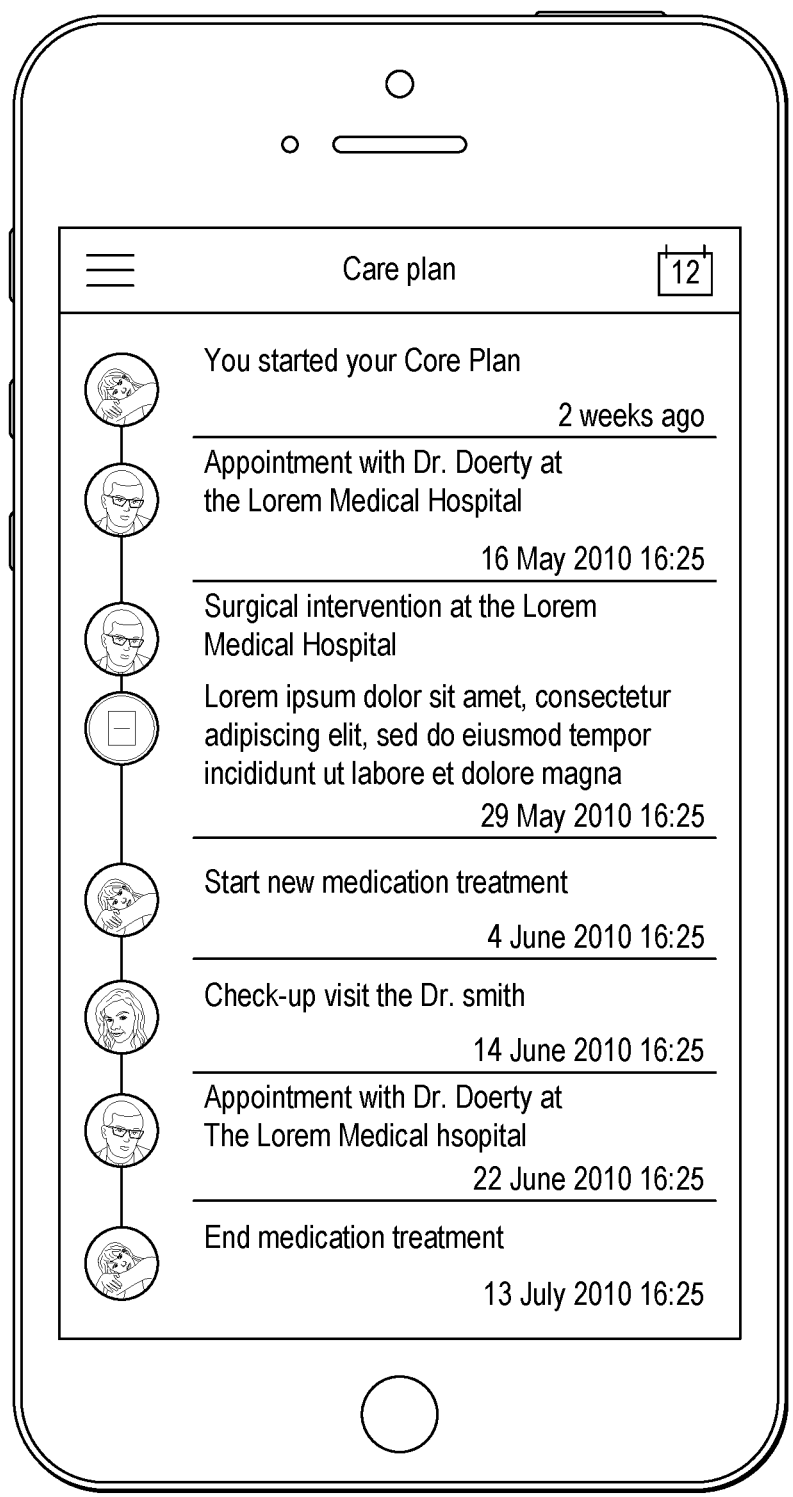
FIG. 15 shows a care compass screenshot.
Figure 16:
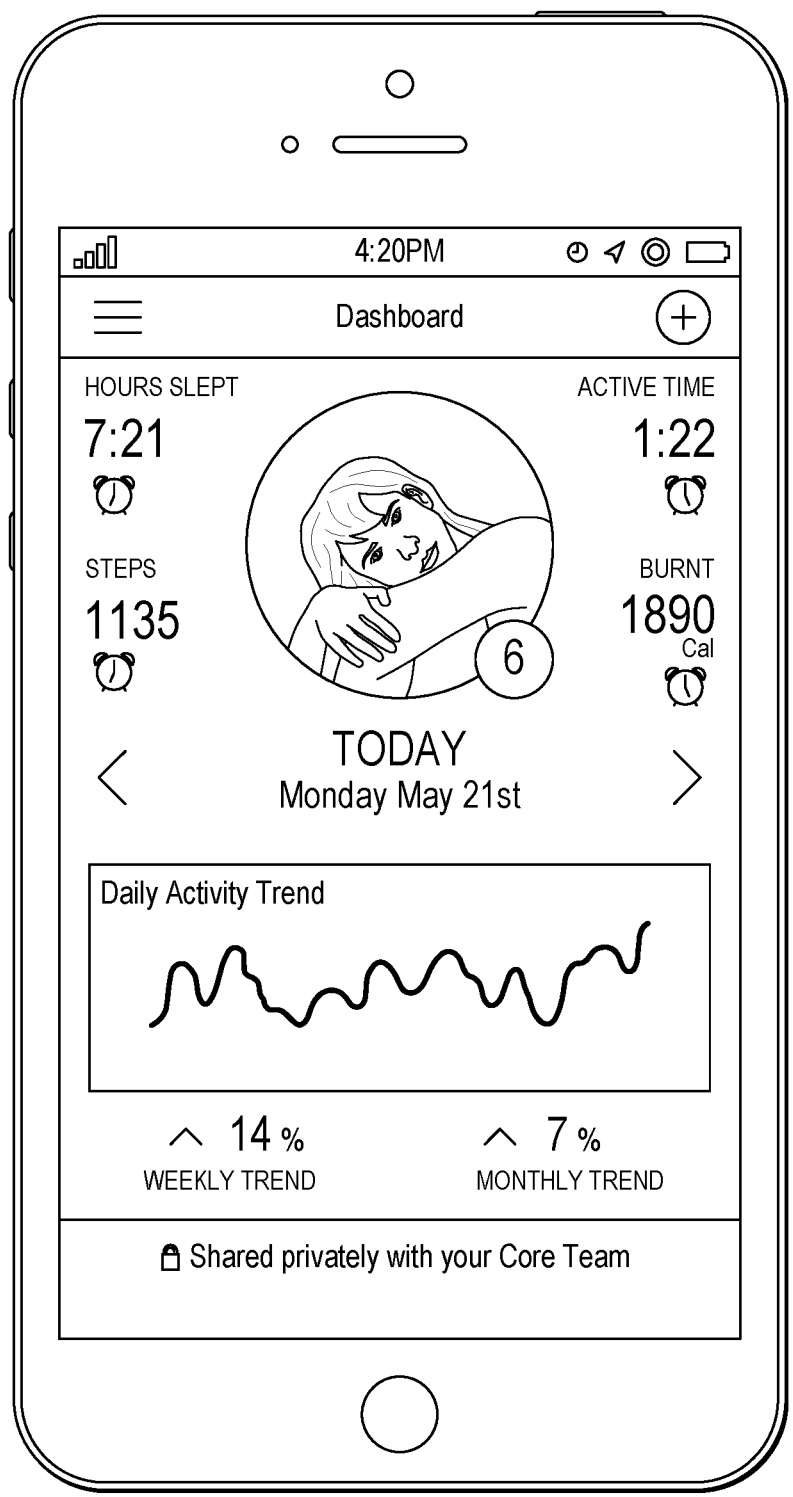
FIG. 16 shows a data dashboard screenshot.

FIG. 15 shows a care compass screenshot. Care compass is maintained by the patient and a caregiving team to display key events, such as diagnosis, appointments, treatment plan/history, surveillance plan/history and events shareable and modifiable by providers within care team. FIG. 16 shows a data dashboard screenshot. This screen displays the user's data from wearable devices. FIG. 16 shows a different aspect of the system architecture in one embodiment. This is another display format wherein the screen displays the patient data from wearable sensors and mobile apps. For example the system integrates with jawbone UP body sensor API to provide activity data tracking. The system also integrates with a foo d diary app such as MyFitnesspal API to provide nutrition data tracking. The sensor and application data may be shared with specific care team to provide insight into patient activity level, wellbeing, and health status.

Figure 17:
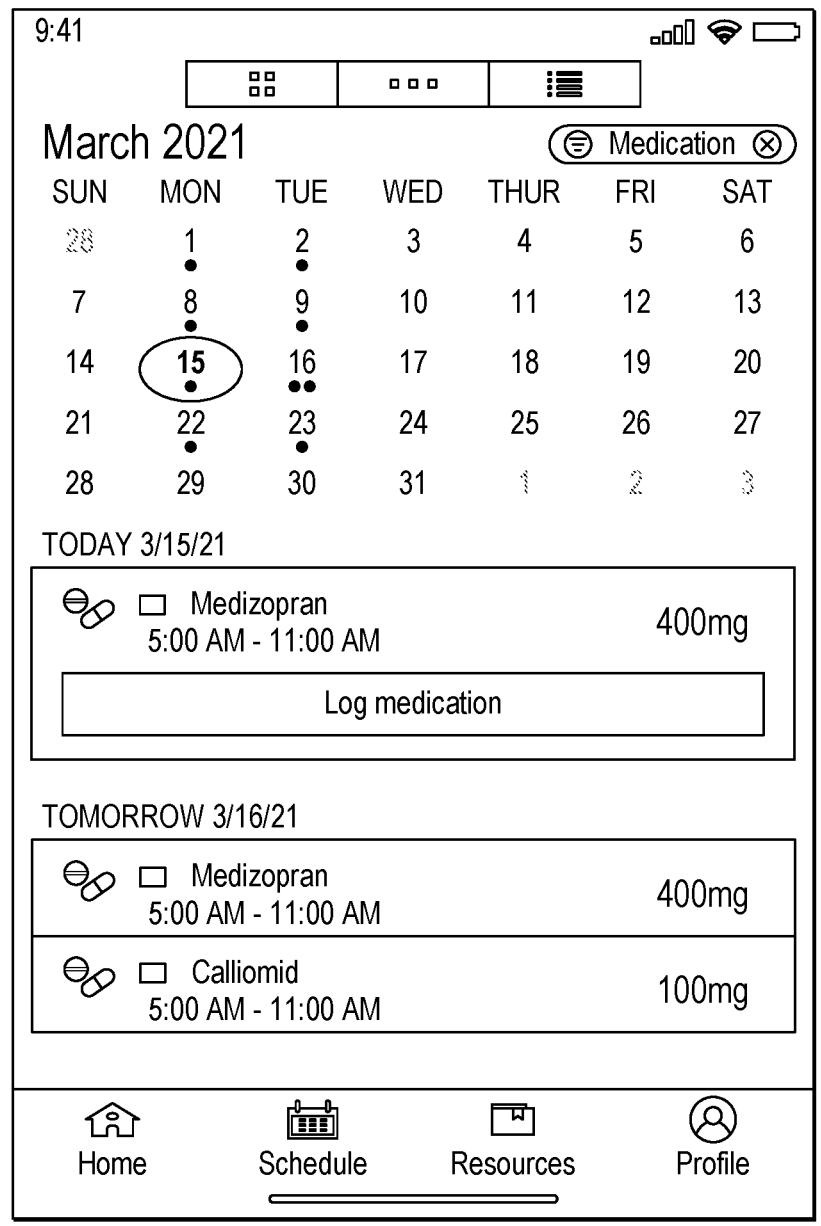
FIG. 17 shows another example of a way to display daily items.

FIG. 17 shows another example of a way to display daily items and encourage progress for either caregiver or patient. The different data, formats, sources all have to be integrated, managed, calculated and displayed. The user input needs to be curated, searched and displayed to different users at different levels. Alarms need to be set for medication reminders. The architecture is complex yet it is done in real time across geographical regions and complying with local authority rules for patient confidentiality and medical directives and guidance.

INDUSTRIAL USE

The instant method and system has broad commercial applicability as a technology solution to improve the ability of informal caregivers to coordinate care with healthcare providers and provide optimal support to cancer survivors and others patients who need home care. The instant system and method includes at least five modules: 1) Secure care team collaboration with secure bi-directional messaging; 2) Medication management; 3) Symptom reporting tracking and management; 4) Condition-specific and general health caregiver and patient education; and 5) Protocol management. The instant system and method platform and underlying architecture enables addition of previously uncontemplated modules, easily configurable role-based dashboards and inclusion of additional roles with minimal programming. Analytical engine based comparative studies will produce rigorously gathered evidence will lead to a substantial reduction in caregiver and provider burden, improved care team communication and coordination, and offers opportunities to improve caregivers' and survivors' mental and physical health and wellbeing, as well as provide important data on the impact of care plans on any long term disease survivorship measures such as outcomes and quality of life.

What is claimed is:

1. A method for providing improved patient care, comprising:
   receiving, at a system comprising a processor, received data that includes smart phone sensor data of a patient and other particular data that includes one or more of (1) medical record data of the patient, (2) physician treatment plan data for the patient from a physician electronic device operated by a physician, (3) medical instrument data, (4) caregiver data from a caregiver electronic device operated by a caregiver, (5) patient input data from a patient electronic device operated by the patient, (6) participant survey data, (7) mobile device data, (8) contextual data, (9) clinical study data, or (10) lab data;
   receiving one or more cohort input commands that identify one or more patient attributes;
   defining a cohort of patients based on identifying the one or more patient attributes in patient cohort data for each of a plurality of particular patients that make up the cohort of patients;
   utilizing an algorithm with the cohort of patients to identify (1) particular smart phone sensor data shared by the cohort of patients and that is indicated in the patient cohort data for each of the plurality of particular patients, and (2) other cohort data shared by the cohort of patients and that is indicated in the patient cohort data for each of the plurality of particular patients;
   analyzing, utilizing the algorithm, the patient cohort data to determine a predicted change in condition for the cohort of patients, wherein the predicted change is condition is determined, based on the analyzing, to correlate with the particular smart phone sensor data shared by the cohort of patients and the other cohort data shared by the cohort of patients; determining that (1) the smart phones sensor data for the patient is substantially similar to the particular smart phone sensor data shared by the cohort of patients, and (2) the other particular data for patient is substantially similar to the other cohort data shared by the cohort of patients;
   determining the predicted change in condition for the patient in response to determining that (1) the smart phones sensor data for the patient is substantially similar to the particular smart phone sensor data shared by the cohort pf patients, and (2) the other particular data for patient is substantially similar to the other cohort data shared by the cohort of patients; and
   presenting the predicted change in condition, where the presenting includes displaying the predicted change in condition on a display unit of one or more of the physician electronic device, the caregiver electronic device, or the patient electronic device.

2. The method of claim 1, further comprising;
   displaying an alert associated with the predicted change in condition on the display unit; and
   displaying, on the display unit, one or more remedial tasks to be implemented based on the predicted change in condition.

3. The method of claim 1, wherein the caregiver, operating the caregiver electronic device, is one of an untrained professional, a family member of the patient, or a trained professional.

4. The method of claim 1, further comprising:
   generating a machine learning model;
   identifying a pattern in the patient cohort data utilizing the machine learning model; and utilizing the pattern to determine the predicted change in condition.

5. The method of claim 4, further comprising:
displaying, on the display unit, a particular patient attribute, wherein the particular patient attribute is displayed as a distribution within the patient cohort data.

6. The method of claim 4, further comprising:
generating, based on user input, an interactive application, wherein the interactive application is utilized to query, in real-time, different patient data.

7. A system for providing improved patient care, comprising:
a processor configured to:
store, at a database, received data that includes smart phone sensor data of a patient and other particular data that includes one or more of (1) medical record data of the patient, (2) physician treatment plan data for the patient from a physician electronic device operated by a physician, (3) medical instrument data, (4) caregiver data from a caregiver electronic device operated by a caregiver, (5) patient input data from a patient electronic device operated by the patient, (6) participant survey data, (7) mobile device data, (8) contextual data, (9) clinical study data, or (10) lab data;
receive one or more cohort input commands that identify one or more patient attributes;
define a cohort of patients based on identifying the one or more patient attributes in patient cohort data for each of a plurality of particular patients that make up the cohort of patients;
utilize an algorithm with the cohort of patients to identify (1) particular smart phone sensor data shared by the cohort of patients and that is indicated in the patient cohort data for each of the plurality of particular patients, and (2) other cohort data shared by the cohort of patients and that is indicated in the patient cohort data for each of the plurality of particular patients;
analyze, utilizing the algorithm, the patient cohort data to determine a predicted change in condition for the cohort of patients, wherein the predicted change is condition is determined, based on the analyzing, to correlate with the particular smart phone sensor data shared by the cohort of patients and the other cohort data shared by the cohort of patients;

determine that the received data for the patent is substantially similar to the patient cohort data;
determine the predicted change in condition for the patient in response to determining that the received data for the patent is substantially similar to the patient cohort data; and
present, in response to the comparing, the predicted change in condition for the patient, where the presenting includes displaying the predicted change of condition on a display unit of one or more of the physician electronic device, the caregiver electronic device, or the patient electronic device.

8. The system of claim 7, wherein the processor is further configured to:
display an alert associated with the predicted change in condition on the display unit.

9. The system of claim 7, wherein the caregiver, operating the caregiver electronic device is one of an un trained professional, a family member of the patient, or a trained professional.

10. The system of claim 7, wherein the processor is further configured to:
display, on the display unit, one or more remedial tasks or recommendations based on the predicted change in condition.

11. The system of claim 7, wherein the processor is further configured to:
generate, based on user input, an interactive application, wherein the interactive application is utilized to query, in real-time, different patient data.

12. The system of claim 7, wherein the processor is further configured to:
generate a machine learning model;
identify a pattern in the patient cohort data utilizing the machine learning model; and
utilize the pattern to determine the prediction.

13. The system of claim 7, wherein the processor is further configured to:
display, on the display unit, a particular patient attribute, wherein the particular patient attribute is displayed as a distribution within the patient cohort data.

* * * * *